US012558117B2

(12) United States Patent
Spodobalski et al.

(10) Patent No.: US 12,558,117 B2
(45) Date of Patent: Feb. 24, 2026

(54) ROTATIONAL ATHERECTOMY DEVICE

(71) Applicant: CLEARSTREAM TECHNOLOGIES LIMITED, Enniscorthy (IE)

(72) Inventors: Artur Spodobalski, Blackwater (IE); Eoin Connaughton, Gorey (IE); Allan Ronan, Enniscorthy (IE)

(73) Assignee: Clearstream Technologies Limited, Enniscorthy (IE)

( * ) Notice: Subject to any disclaimer, the term of this patent is extended or adjusted under 35 U.S.C. 154(b) by 121 days.

(21) Appl. No.: 18/706,655

(22) PCT Filed: Nov. 3, 2021

(86) PCT No.: PCT/EP2021/080474
§ 371 (c)(1),
(2) Date: May 1, 2024

(87) PCT Pub. No.: WO2023/078539
PCT Pub. Date: May 11, 2023

(65) Prior Publication Data
US 2024/0415534 A1     Dec. 19, 2024

(51) Int. Cl.
| | |
|---|---|
| *A61B 17/3207* | (2006.01) |
| *A61B 17/00* | (2006.01) |
| *A61B 17/32* | (2006.01) |

(52) U.S. Cl.
CPC ............... *A61B 17/320758* (2013.01); *A61B 17/320725* (2013.01); *A61B 2017/00017* (2013.01);
(Continued)

(58) Field of Classification Search
CPC ...... A61B 17/320758; A61B 17/32075; A61B 17/3207; A61B 17/320725; A61B 17/320783
(Continued)

(56) References Cited

U.S. PATENT DOCUMENTS 5,554,163 A * 9/1996 Shturman ...... A61B 17/320783
                                              606/159
8,747,332 B2   6/2014 Noriega
(Continued)

FOREIGN PATENT DOCUMENTS

WO     2016108860 W     7/2016

OTHER PUBLICATIONS

International Search Report and Written Opinion dated Jul. 12, 2022 pertaining to PCT/EP2021/080474 filed Nov. 3, 2021.

*Primary Examiner* — Tuan V Nguyen
(74) *Attorney, Agent, or Firm* — Dinsmore & Shohl LLP

(57) ABSTRACT

A rotational atherectomy device for cutting or abrading tissue. The atherectomy device comprises a rotatable drive shaft (120) having a longitudinal axis and comprising one or more internal guiding tracks (121) extending along the length of the drive shaft (120). The rotational atherectomy device further comprises one or more flexible shafts (111, 113) arranged to be longitudinally moveable along a respective internal guiding track, and an abrasive head (110) disposed at the distal end of the one or more flexible shafts (111, 113). The abrasive head (110) comprises one or more abrasive elements (111), each abrasive element connected to a respective flexible shaft (111, 113). The one or more guiding tracks (121) are arranged such that distal movement of the one or more flexible shafts (111, 113) causes the abrasive head (110) to move from a radially contracted configuration to a radially expanded configuration.

21 Claims, 4 Drawing Sheets

(52) U.S. Cl.
CPC ............... *A61B 2017/00398* (2013.01); *A61B 2017/320008* (2013.01)

(58) Field of Classification Search
USPC ........................................................ 606/159
See application file for complete search history.

(56) References Cited

U.S. PATENT DOCUMENTS

| | | |
|---|---|---|
| 9,216,034 B2 * | 12/2015 | Avneri ........... A61B 17/320758 |
| 2002/0077638 A1 | 6/2002 | Kadavy et al. |
| 2005/0261674 A1 | 11/2005 | Nobis et al. |
| 2008/0033423 A1 | 2/2008 | Peacock |
| 2009/0306689 A1 | 12/2009 | Welty et al. |
| 2010/0094320 A1 | 4/2010 | Arat |
| 2012/0197277 A1 * | 8/2012 | Stinis ............. A61B 17/320758 |
| | | 606/190 |
| 2014/0277002 A1 * | 9/2014 | Grace ................ A61B 17/2202 |
| | | 606/159 |
| 2015/0127032 A1 * | 5/2015 | Lentz ............. A61B 17/320708 |
| | | 606/159 |
| 2015/0359595 A1 | 12/2015 | Oren et al. |
| 2017/0065396 A1 | 3/2017 | Look et al. |
| 2018/0256196 A1 | 9/2018 | Nishio et al. |
| 2020/0197033 A1 | 6/2020 | Pasquino et al. |

* cited by examiner

ROTATIONAL ATHERECTOMY DEVICE

CROSS REFERENCE TO RELATED APPLICATION

This application is a U.S. National Phase of International Application No. PCT/EP2021/080474, filed Nov. 3, 2021, which is incorporated herein by reference in its entirety.

TECHNICAL FIELD

The present disclosure relates to a rotational atherectomy device for cutting or abrading tissue, and a method of cutting or abrading tissue using an atherectomy device.

BACKGROUND

Atherosclerosis is a condition where calcified plaque deposits in the walls of a blood vessel lead to narrowing of the blood vessel and increased blood pressure. In severe cases, this can result in peripheral artery disease, coronary artery disease, tissue death or stroke.

Atherosclerosis can be treated in a number of ways such as by angioplasty, where a balloon is used to force the expansion of the blood vessel to allow improved blood flow, a vascular bypass, where a surgical procedure is performed to redirect the blood flow to circumvent the diseased area of the blood vessel, or atherectomy.

Atherectomy is a non-surgical procedure to open blocked blood vessels using a device at the distal end of a catheter to cut or grind atherosclerotic plaque from the walls of the blood vessel. Atherectomy devices can generally be classified into four different types: orbital, rotational, laser and directional.

A rotational atherectomy device uses a rotating abrasive head to cut or grind the atherosclerotic plaque from the walls of the blood vessel. A number of existing rotational atherectomy devices incorporate an abrasive head of fixed diameter. In order to treat larger diameter vessels, the abrasive head is offset towards one side of the vessel wall and the lesion is treated with multiple axial passes. This makes the treatment procedure longer and more complex. A type of expandable rotational atherectomy device is disclosed, for example, in US 2009/0306689 A1 where the abrasive head comprises a number of abrasive elements which extend under the centrifugal force of the rotating drive shaft. However, this type of expanding atherectomy device does not allow a physician to easily adjust the amount of expansion of the abrasive head.

There is hence a need in the art for a new type of rotational atherectomy device which allows controlled and precise expansion of the abrasive head and therefore reduce the overall treatment time as larger vessels can be treated in fewer axial passes of the abrasive head.

SUMMARY

In a first aspect of the present disclosure, there is provided a rotational atherectomy device for cutting or abrading tissue. The atherectomy device comprises a rotatable drive shaft having a longitudinal axis and comprising one or more internal guiding tracks extending along the length of the drive shaft, one or more flexible shafts arranged to be longitudinally moveable along a respective internal guiding track, and an abrasive head disposed at the distal end of the one or more flexible shafts. The abrasive head comprises one or more abrasive elements. Each abrasive element is connected to a respective flexible shaft. The one or more guiding tracks are arranged such that distal movement of the one or more flexible shafts causes the abrasive head to move from a radially contracted configuration to a radially expanded configuration.

In some embodiments, this may allow the abrasive head to be expanded in a precise and controlled manner. In some embodiments, this may reduce the overall treatment time and make the treatment procedure simpler.

Throughout this disclosure, the term 'abrasive head' is used to refer to a component of the atherectomy device which comprises multiple elements for mechanically removing tissue from the inside of a vessel.

Throughout this disclosure, the term 'abrasive element' includes any element which is suitable for mechanically removing tissue from the inside of a vessel. This may be, for example, through cutting, grinding or scraping.

Throughout this disclosure, the term 'radially expanded configuration' means a configuration of the abrasive head where the one or more abrasive elements are disposed further from the longitudinal axis than in a 'radially contracted configuration'.

A distal end of the one or more guiding tracks may be bent at least partly in a radially outward direction.

In some embodiments, this may allow the abrasive head to more easily move between the radially contracted configuration to the radially expanded configuration.

The radial extent of the abrasive head during rotation may be greater in the radially expanded configuration than in the radially contracted configuration.

In some embodiments, this may allow a greater surface area to be abraded in one axial pass.

The one or more abrasive elements may comprise a cutting surface. The one or more abrasive elements may comprise an abrasive surface. The one or more abrasive elements may comprise both a cutting and an abrasive surface.

In some embodiments, this may allow the abrasive head to more efficiently abrade or cut calcified plaque from the blood vessel walls.

The rotational atherectomy device may comprise two internal guiding tracks, and two flexible shafts. The abrasive head may comprise a first abrasive element and a second abrasive element.

In some embodiments, this may result in better cutting or abrading action of the abrasive head.

The first abrasive element and the second abrasive element may be disposed on opposite sides of the longitudinal axis.

In some embodiments, this may result in a symmetrical abrasive head which allows more stable rotation and therefore better cutting or abrading of the tissue.

The first and second abrasive elements may both have a greater radial extent in the radially expanded configuration than in the radially contracted configuration.

In some embodiments, this may allow a greater surface area to be abraded in one axial pass The one or more abrasive elements may extend distally from the drive shaft in the radially contracted position and the radially expanded position.

In some embodiments, this may allow the abrasive head to cut or abrade tissue in the radially contracted configuration and the radially expanded configuration.

The drive shaft may further comprise a guidewire lumen for accommodating a guidewire.

In some embodiments, this may allow a guidewire to be disposed in the guidewire lumen to guide the atherectomy device to the treatment area.

The rotational atherectomy device may further comprise a rotational motor for providing rotation to the drive shaft and the abrasive head.

In some embodiments, this may allow the rotation of the abrasive head to be more efficiently powered by a motor.

A proximal section of the one or more flexible shafts may form a single inner shaft. The rotational motor may be coupled to the inner shaft.

The rotational motor may be coupled to the drive shaft.

The rotational atherectomy device may further comprise a control unit for controlling the speed of rotation of the drive shaft.

In some embodiments, this may allow a user to vary the speed of rotation of the abrasive head to adapt it to different situation types and thereby achieve a more controlled cutting or abrading action.

The one or more internal guiding tracks may accommodate the respective one or more flexible shafts such that the one or more flexible shafts cannot rotate with respect to the drive shaft.

The one or more internal guiding tracks may have a T-shaped cross-section.

The one or more flexible shafts may have a corresponding T-shaped cross-section.

In some embodiments, this may allow the one or more flexible shafts to easily move axially with respect to the drive shaft but prevents respective rotation between the one or more flexible shafts and the drive shaft.

The one or more internal guiding tracks may have a triangular cross-section.

The one or more flexible shafts have a corresponding triangular cross-section.

In some embodiments, this may allow the one or more flexible shafts to easily move axially with respect to the drive shaft but prevents respective rotation between the one or more flexible shafts and the drive shaft.

The rotational atherectomy device may further comprise an expansion control mechanism for moving the one or more flexible shafts longitudinally with respect to the drive shaft to thereby move the abrasive head between the radially contracted configuration and the radially expanded configuration.

In some embodiments, this may allow a user to easily control the amount of expansion of the abrasive head.

The expansion control mechanism may be disposed at the proximal end of the drive shaft.

A proximal section of the one or more flexible shafts may form a single inner shaft and the rotational motor may be connected to the inner shaft.

In some embodiments, this may allow a simple connection between the motor and the one or more flexible shafts.

The expansion control mechanism may be a rack and pinion mechanism configured to move the motor in a longitudinal direction.

In some embodiments, this may provide a simple mechanism for a user to control the amount of expansion.

The rotational motor may be connected to the one or more flexible shafts. The rack and pinion mechanism may be configured to move the motor in a longitudinal direction.

The expansion control mechanism may comprise a screw and bolt mechanism for moving the motor in a longitudinal direction.

In some embodiments, this may provide a simple mechanism for a user to control the amount of expansion.

The rotational atherectomy device may further comprise a catheter shaft, wherein the rotatable drive shaft is disposed within the catheter shaft.

In some embodiments, this may protect the drive shaft from external influences and allow the atherectomy device to be delivered to the treatment area more easily. In some embodiments, this also protects the blood vessel from the rotating drive shaft.

In a second aspect of the present disclosure, there is provided a method of cutting or abrading tissue using an atherectomy device. The atherectomy device comprises a rotatable drive shaft having one or more internal guiding tracks, one or more flexible shafts arranged to be longitudinally moveable along a respective internal guiding track, and an abrasive head having one or more abrasive elements disposed at the distal end of the one or more flexible shafts. The method comprises: introducing the atherectomy device into a blood vessel, advancing the atherectomy device to a position in the blood vessel where tissue is to be cut or abraded, rotating the abrasive head to cut or abrade the tissue, expanding the abrasive head by distally moving the one or more flexible shafts to move the abrasive head to from a radially contracted configuration to a radially expanded configuration.

In some embodiments, this may result in a method which allows an abrasive head of an atherectomy device to be expanded in a precise and controlled manner. In some embodiments, this may reduce the overall treatment time and make the treatment procedure simpler.

BRIEF DESCRIPTION OF THE DRAWINGS

To enable better understanding of the present disclosure, and to show how the same may be carried into effect, reference will now be made, by way of example only, to the accompanying drawings, in which.

DETAILED DESCRIPTION

Figure 1:
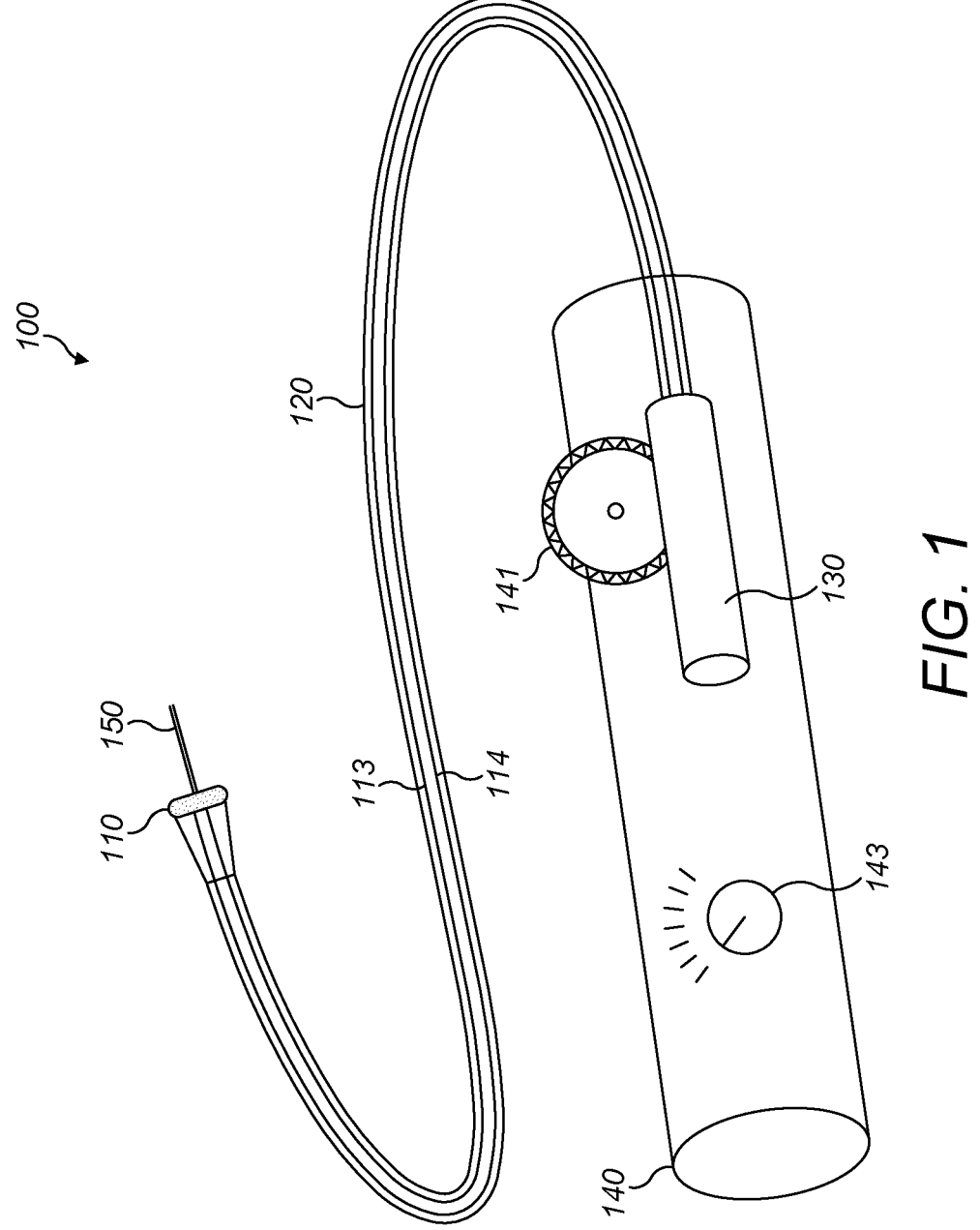
FIG. 1 shows a rotational atherectomy device according to the present disclosure.

FIG. 1 shows a rotational atherectomy device 100 for removing calcified plaque from a vessel. The rotational atherectomy device 100 comprises an abrasive head 110 disposed at the distal end of an elongated drive shaft 120. The drive shaft 120 is flexible so that it can be inserted and navigated through a tortuous vessel anatomy. The abrasive head 110 may comprise a number of abrasive elements such as, but not limited to, abrasive elements 111, 112 which, when rotated, can cut or scrape calcified plaque from the inside of a vessel wall. The abrasive head 110 is expandable from a radially contracted configuration to a radially expanded configuration in order to easily allow a larger diameter vessel to be treated. The radial extent of the abrasive head 110 is greater in the radially expanded configuration than in the radially contracted configuration.

As noted above, in embodiments the abrasive head 110 may include one or more abrasive elements such as a first abrasive element 111 and a second abrasive element 112. The first abrasive element 111 is connected to the distal end of a first flexible shaft 113 and the second abrasive element 112 is connected to the distal end of a second flexible shaft 114. Each flexible shaft 113, 114 may be disposed within the drive shaft 120 and extends along the length of the drive shaft 120.

The drive shaft 120 and the flexible shafts 113, 114 may be connected at their proximal ends to a hub 140. The hub 140 may include a rotational motor 130 which can impart rotational motion to the drive shaft 120 and the abrasive head 110.

The hub 140 may also include an expansion control mechanism which is shown in the form of rack and pinion mechanism 141, for example. This allows a physician to control the amount of expansion of the abrasive head 110 from outside a patient's body by turning the pinion. The hub also may further include a rotation control unit in the form of a dial 143, for example, which can be turned to set the speed of rotation of the motor 130 and thereby control the speed of rotation of the abrasive head 110.

In order to remove calcified plaque from a vessel of a patient, first a suitable access site may be identified. A guidewire 150 may then introduced into the vessel through the access site and advanced to the treatment site. The treatment site may be, for example, a heavily calcified section of the vessel where the vessel is significantly narrowed or even fully blocked such that blood flow through the vessel is significantly reduced. The drive shaft 120 and abrasive head 110 of the atherectomy device 100 are then introduced into the blood vessel over the guidewire 150 and through the access site. The drive shaft 120 and abrasive head 110 may be disposed within a catheter or sheath for introduction into the vessel and advancement to the treatment site.

The abrasive head 110 may then be advanced over the guidewire 150 to the treatment area. Once the abrasive head 110 is positioned at the treatment site, the physician can turn on the rotational motor 130 which will cause the drive shaft 120 and abrasive head 110 to rotate. The rotation will cause the abrasive head 110 to cut or scrape calcified plaque from the inside of the vessel wall. The speed of rotation of the abrasive head can be controlled by turning the dial 143 of the rotation control unit. Furthermore, the physician can accurately adjust the radial extent or expansion of the abrasive head 110 through the expansion control mechanism, by rotating the pinion of the rack and pinion mechanism 141, for example. This allows controlled and precise expansion of the abrasive head 110 and therefore reduce the overall treatment time as larger vessels can be treated in fewer axial passes of the abrasive head 110.

An embodiment of an expansion mechanism of the abrasive head 110 is illustrated in more detail in FIG. 2.

Figure 2A:
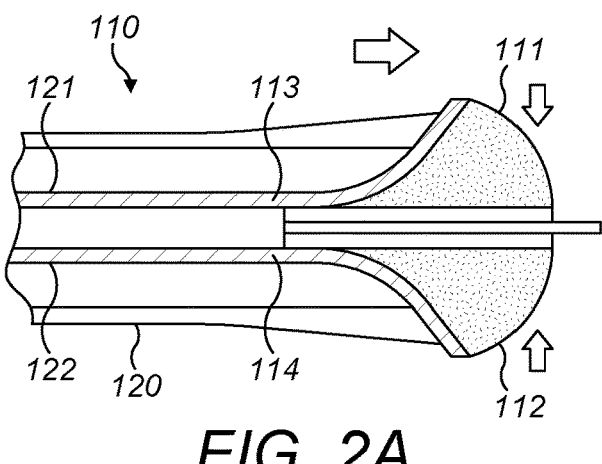
FIGS. 2A-C show a sequence of side views of the abrasive head of the rotational atherectomy device of FIG. 1 moving from a retracted configuration to an expanded configuration.

FIG. 2A shows a side view of the abrasive head 110 in the radially contracted configuration. In the present embodiment, the abrasive head 110 includes the first abrasive element 111 connected to the distal end of the first flexible shaft 113 and the second abrasive element 112 connected to the distal end of the second flexible shaft 114.

The first abrasive element 111 and second abrasive element 112 each comprise a cutting surface for cutting or an abrasive surface or grinding calcified plaque from the inside of the vessel wall. The abrasive elements 111, 112 may be made from a number of materials such as, but not limited to, a cobalt base alloy, oxidised zirconium, or tungsten. The cutting surface may comprise a number of sharp edges which cut the plaque from the walls of the vessel. The abrasive surface may be a rough surface which can grind away the plaque from the walls of the vessel through friction. The abrasive elements 111, 112 may each also comprise a combination of cutting surfaces and abrasive surfaces.

The first abrasive element 111 and the second abrasive element 112 may be disposed on opposite sides of the longitudinal axis of the drive shaft 120. In the embodiment of FIG. 2, the abrasive head 110 is shown as having two abrasive elements. However, the abrasive head 110 may comprise more than two abrasive elements, with each abrasive element connected to its own respective flexible shaft.

The first flexible shaft 113 and the second flexible shaft 114 extend within the drive shaft 120 from the distal abrasive head 110 to the proximal hub 140. The drive shaft 120 may include one or more internal guiding tracks. For example, the drive shaft 120 may include a first internal guiding track 121 for accommodating the first flexible shaft 113 and a second internal guiding track 122 for accommodating the second flexible shaft 114. The first flexible shaft 113 and the second flexible shaft 114 may be longitudinally moveable along the respective first and second internal guiding tracks 121, 122. The longitudinal 1 movement of the first and second flexible shaft 113, 114 can be controlled by the physician through the expansion control mechanism in the hub 140, for example, by turning the pinion on the rack and pinion mechanism 141.

Figure 3A:
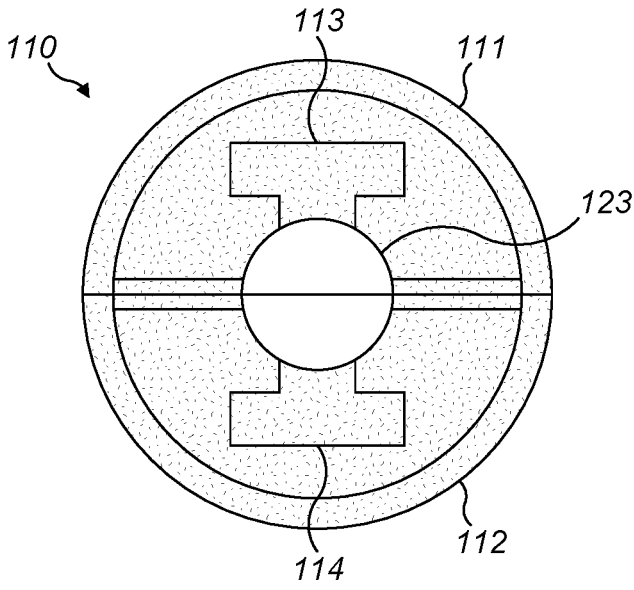
FIGS. 3A and B show a front view of the distal abrasive head of the rotational atherectomy device of FIG. 1 in the contracted configuration and the expanded configuration.
Figure 3B:
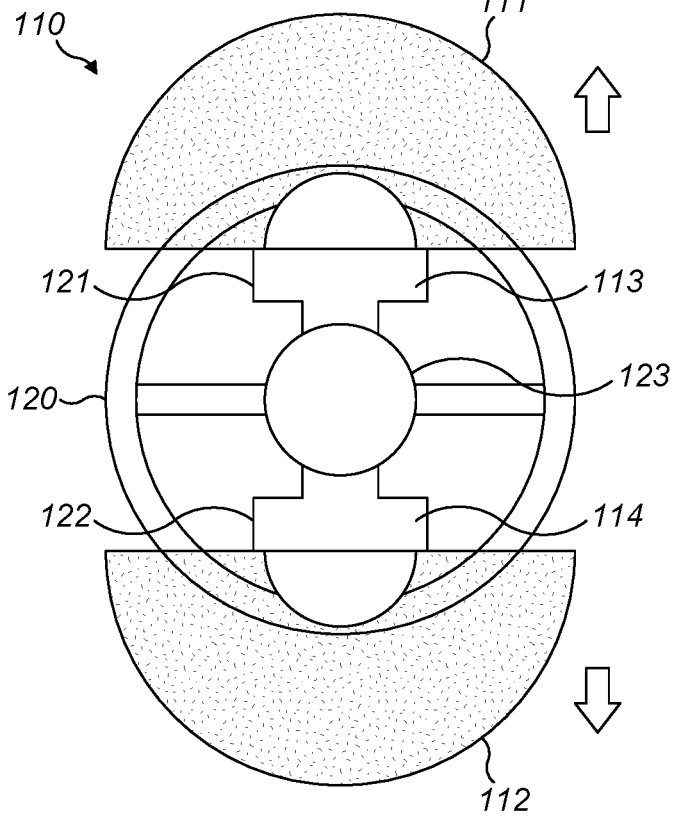

The first and second flexible shaft 113, 114 both may have a T-shaped cross section, which is shown more clearly in FIGS. 3A and 3B. The first and second internal guiding tracks 121, 122 have a corresponding T-shaped cross section. The shape of the cross section prevents the first and second flexible shafts 113, 114 from turning or rotating with respect to the drive shaft 120 while still allowing longitudinal movement of the flexible shafts 113, 114 with respect to the drive shaft 120.

The first and second guiding tracks 121, 122 may form a radially out-ward curved path towards the distal end of the drive shaft 120. This results in the first and second flexible shaft 113, 114 following the curvature of their respective guiding track and bending radially outward towards their distal end.

Figure 2B:
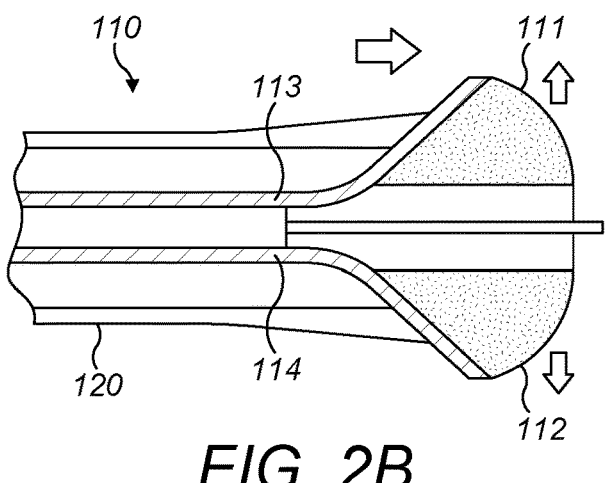

As shown in FIG. 2B, if the first and second flexible shaft 113, 114 are moved distally, the curvature of the guiding tracks 121, 122 results in the distal end of the flexible shafts 113, 114 moving radially outwardly. The abrasive elements 111, 112, which are attached to the distal end of the flexible shafts 113, 114 thereby also move radially outwardly and the diameter of the abrasive head 110 is expanded.

Figure 2C:
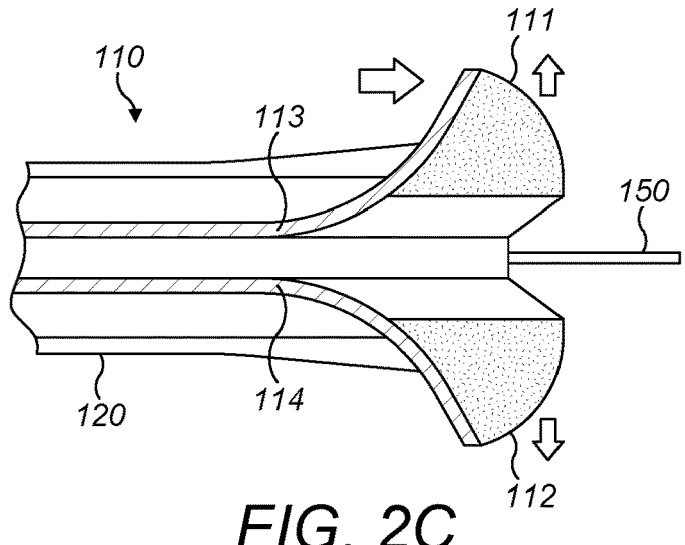

Further distal movement of the flexible shafts 113, 114 will result in further radial expansion of the abrasive elements 111, 112, as shown in FIG. 2C. The amount of expansion can be controlled by controlling the amount of distal movement of the flexible shafts 113, 114 through the expansion control mechanism in the hub 140. Both abrasive elements 111, 112 extend distally from the drive shaft 120 in the radially contracted position of FIG. 2A and the radially expanded position of FIG. 2C. This allows the abrasive head 110 to rotate and be used in both configurations.

FIG. 3A shows the abrasive head 110 in the contracted configuration from a distal front view. This shows the T-shaped cross section of the first and second flexible shaft 113, 114 and the corresponding T-shaped cross section of the first and second guiding tracks 121, 122. The first and second abrasive elements 111, 112 may be disposed on opposite sides of the longitudinal axis of the drive shaft 120.

The drive shaft 120 may further include a guidewire lumen 123 for accommodating the guidewire 150.

In the radially expanded configuration shown in FIG. 3B, the first and second abrasive elements 111, 112 have moved radially away from each other in opposite directions. As depicted in the present embodiment, the radial extent of the abrasive head 110 is greater in the radially expanded configuration of FIG. 3B than it is in the radially contracted configuration of FIG. 3A.

Figure 4A:
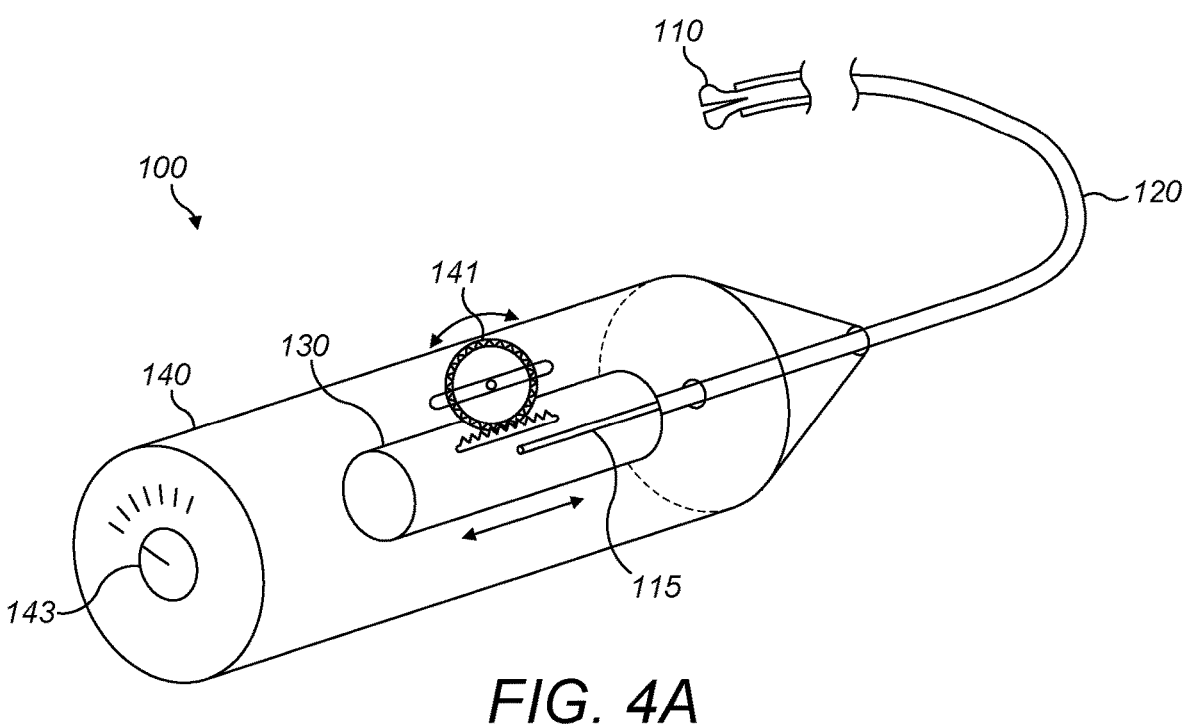
FIGS. 4A and B show two variations of a hub and expansion control mechanism for the rotational atherectomy device.
Figure 4B:
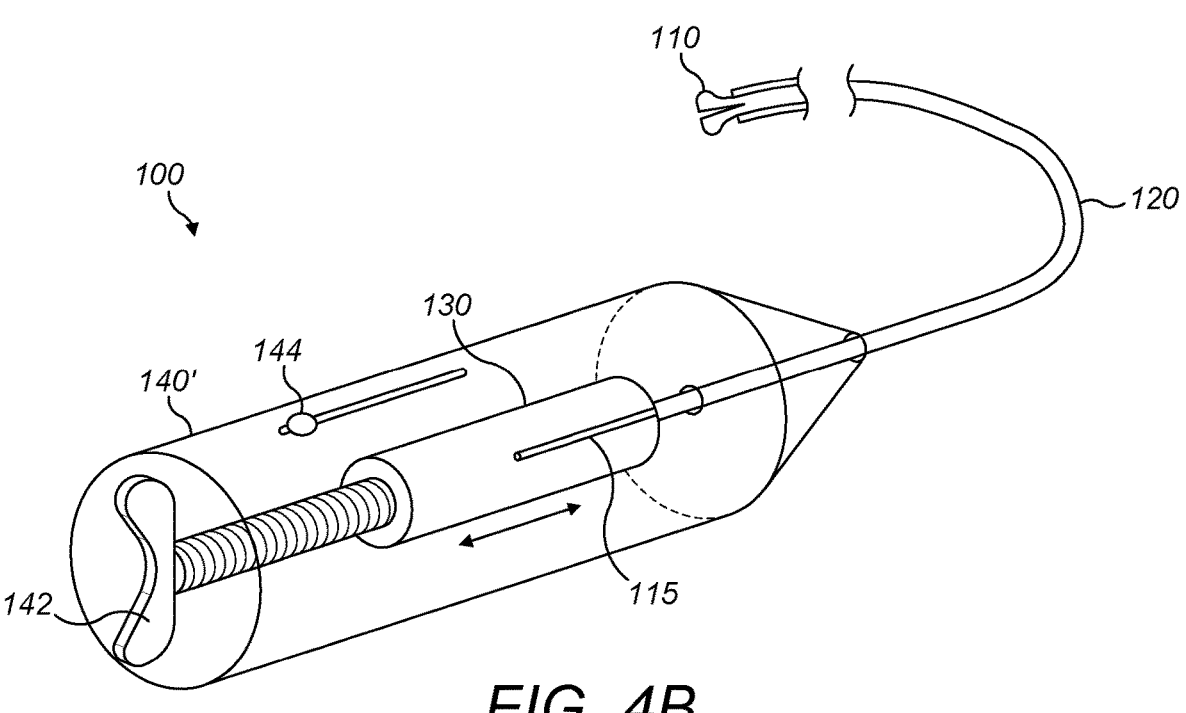

FIGS. 4A and 4B illustrate two different variations of the hub 140 and the expansion control mechanism for controlling the amount of expansion of the abrasive head 110.

FIG. 4A shows a hub 140 similar to that of FIG. 1 comprising a dial 143 as a rotation control unit for setting the speed of rotation of the motor 130 and thereby the speed of rotation of the abrasive head 110. The hub 140 may further include a rack and pinion mechanism 141 as an expansion control mechanism for controlling the amount of radial expansion of the abrasive head 110. A proximal section of the first flexible shaft 111 and second flexible shaft 112 may be joined to form a combined inner shaft 115 which is connected to the rotational motor 130. The inner shaft 115 is arranged such that it can move longitudinally with respect to the drive shaft 120 but can only rotate together with the drive shaft 120. Rotation of the inner shaft 115 will therefore result in rotation of the drive shaft 120 and the abrasive head 110.

The linear rack of the rack and pinion mechanism 141 may be attached to the outside of the motor 130 and engages the circular pinion. The pinion may be accessible from the outside of the hub and can be rotated to move the motor 130 in a linear fashion. Moving the motor 130 with the inner shaft 115 distally causes flexible shafts 113, 114 to move distally relative to the drive shaft 120 and thereby causes the abrasion head 110 to expand radially. Moving the motor with the inner shaft 115 proximally causes flexible shafts 113, 114 to move proximally relative to the drive shaft 120 and the abrasion head 110 to radially contract.

FIG. 4B shows a variation of a hub 140'. Similar to FIG. 4A, a proximal section of the first flexible shaft 111 and second flexible shaft 112 may be joined to form a combined inner shaft 115 which is connected to the rotational motor 130. The inner shaft 115 is arranged such it can move longitudinally with respect to the drive shaft 120 but can only rotate together with the drive shaft 120. Rotation of the inner shaft 115 will therefore result in rotation of the drive shaft 120 and the abrasive head 110.

In order to move the motor 130 distally and proximally with respect to the drive shaft 120 and thereby control the expansion of the abrasive head 110, hub 140' may include an expansion control mechanism in the form of a screw mechanism 142 which is attached to the proximal end of the motor. Rotation of the screw mechanism 142 in a first direction will move the motor with the inner shaft 115 distally and thereby cause radial expansion of the abrasive head 110. Similarly, rotation of the screw mechanism 142 in a second opposite direction will move the motor with the inner shaft 115 in a proximal direction and result in radial contraction of the abrasive head 110. The screw mechanism 142 allows very fine and precise control of the expansion of the abrasion head and prevents backlash.

The hub 140' may further include a rotation control unit in the form of a slider 144 which can be used to control the speed of rotation of the motor 130 and therefore the speed of rotation of the abrasive head 110.

Various modifications will be apparent to those skilled in the art.

As noted above, the abrasive head 110 may comprise more than two abrasive elements. Each of the abrasive elements may be connected to its own flexible shaft. For example, the abrasive head may comprise three abrasive elements which are disposed at 120-degree angles around the abrasive head 110.

The abrasive head 110 may only comprise one abrasive element.

The first and second flexible shaft 111, 112 may have a differently shaped cross-section. The first and second guiding tracks 121, 122 may have a corresponding differently shaped cross section. For example, the first and second flexible shaft 111, 112 may have a triangular cross-section and the first and second guiding tracks 121, 122 may have a corresponding triangular cross section.

Any cross-section which of the internal guiding tracks 121, 122 and corresponding cross section of the flexible shaft 111, 112 which prevents the flexible shafts 111, 112 from rotating with respect to the drive shaft can be used.

The drive shaft 120 may not comprise a guidewire lumen 123.

The rotational control unit is not limited to the dial 143 or the slider 144 but may take other forms, such as a display with buttons, for example.

The atherectomy device 100 may not comprise a rotational control unit.

The expansion control mechanism is not limited to a rack and pinion mechanism 141 or a screw mechanism 142 but may take other forms, such as a linear slider or a plunger.

The atherectomy device may not comprise an expansion control mechanism but rather the flexible shafts 111, 112 may simply be moved with respect to the drive shaft 120 by hand.

The internal guiding tracks 121, 122 may not bend outwardly towards the distal end of the drive shaft 120. Rather, the flexible shafts 111, 112 may have a pre-bent distal portion which means that they deflect laterally as they leave the respective internal guiding track, thereby resulting in the abrasive head expanding radially.

The atherectomy device may further comprise a sheath or catheter which encloses or accommodates the drive shaft.

All of the above are fully within the scope of the present disclosure and are considered to the basis for alternative embodiments in which one or more combinations of the above described features are applied, without limitation to the specific combination disclosed above.

In light of this, there will be many alternatives which implement the teaching of the present disclosure. It is expected that one skilled in the art will be able to modify and adapt the above disclosure to suit its own circumstances and requirements within the scope of the present disclosure, while retaining some or all technical effects of the same, either disclosed or derivable from the above, in light of his common general knowledge in this art. All such equivalents, modifications or adaptations fall within the scope of the present disclosure.

The invention claimed is:

1. A rotational atherectomy device for cutting or abrading tissue, the atherectomy device comprising:
    a rotatable drive shaft having a longitudinal axis and comprising one or more internal guiding tracks extending along the length of the drive shaft;
    one or more flexible shafts arranged to be longitudinally moveable along a respective internal guiding track; and an abrasive head disposed at the distal end of the one or more flexible shafts, the abrasive head comprising one or more abrasive elements, each abrasive element connected to a respective flexible shaft;

wherein a distal end of the one or more guiding tracks bends at least partly in a radially outward direction such that distal movement of the one or more flexible shafts causes the abrasive head to move from a radially contracted configuration to a radially expanded configuration.

2. The rotational atherectomy device of claim 1, wherein the one or more abrasive elements comprises a cutting surface and/or an abrasive surface.

3. The rotational atherectomy device of claim 1, comprising:

two internal guiding tracks; and two flexible shafts, wherein the abrasive head comprises a first abrasive element and a second abrasive element.

4. The rotational atherectomy device of claim 3, wherein the first abrasive element and the second abrasive element are disposed on opposite sides of the longitudinal axis.

5. The rotational atherectomy device of claim 3, wherein both the first and second abrasive elements have a greater radial extent in the radially expanded configuration than in the radially contracted configuration.

6. The rotational atherectomy device of claim 1, wherein the one or more abrasive elements extend distally from the drive shaft in the radially contracted position and the radially expanded position.

7. The rotational atherectomy device of claim 1, wherein the drive shaft further comprises a guidewire lumen for accommodating a guidewire.

8. The rotational atherectomy device of claim 1, further comprising a rotational motor for providing rotation to the drive shaft and the abrasive head.

9. The rotational atherectomy device of claim 8, wherein a proximal section of the one or more flexible shafts forms a single inner shaft, and the rotational motor is coupled to the inner shaft.

10. The rotational atherectomy device of claim 8, wherein the rotational motor is coupled to the drive shaft.

11. The rotational atherectomy device of claim 1, further comprising a control unit for controlling the speed of rotation of the drive shaft.

12. The rotational atherectomy device of claim 1, wherein the cross-sectional shape of the one or more internal guiding tracks and the cross-sectional shape of the respective one or more flexible shafts prevent the one or more flexible shafts from rotating with respect to the drive shaft.

13. The rotational atherectomy device of claim 1, wherein the one or more internal guiding tracks have a T-shaped cross-section.

14. The rotational atherectomy device of claim 13, wherein the one or more flexible shafts have a corresponding T-shaped cross-section.

15. The rotational atherectomy device of claim 1, further comprising an expansion control mechanism for moving the one or more flexible shafts longitudinally with respect to the drive shaft to thereby move the abrasive head between the radially contracted configuration and the radially expanded configuration.

16. The rotational atherectomy device of claim 15, wherein the expansion control mechanism is disposed at the proximal end of the drive shaft.

17. The rotational atherectomy device of claim 15, wherein a proximal section of the one or more flexible shafts forms a single inner shaft and wherein the rotational motor is connected to the inner shaft.

18. The rotational atherectomy device of claim 15, wherein the expansion control mechanism is a rack and pinion mechanism configured to move the motor in a longitudinal direction.

19. The rotational atherectomy device of claim 15, wherein the expansion control mechanism comprises a screw mechanism for moving the motor in a longitudinal direction.

20. The rotational atherectomy device of claim 1, further comprising a catheter shaft, wherein the rotatable drive shaft is disposed within the catheter shaft.

21. A method of cutting or abrading tissue using an atherectomy device comprising a rotatable drive shaft having one or more internal guiding tracks, one or more flexible shafts arranged to be longitudinally moveable along a respective internal guiding track, and an abrasive head having one or more abrasive elements disposed at the distal end of the one or more flexible shafts, wherein a distal end of the one or more guiding tracks bends at least partly in a radially outward direction such that distal movement of the one or more flexible shafts causes the abrasive head to move from a radially contracted configuration to a radially expanded configuration, the method comprising:

introducing the atherectomy device into a blood vessel;

advancing the atherectomy device to a position in the blood vessel where tissue is to be cut or abraded;

rotating the abrasive head to cut or abrade the tissue; and expanding the abrasive head by distally moving the one or more flexible shafts to move the abrasive head to from a radially contracted configuration to a radially expanded configuration.

* * * * *